United States Patent [19]

Ridolfo

[11] 4,355,029

[45] Oct. 19, 1982

[54] COMBINATION THERAPY FOR RHEUMATOID ARTHRITIS

[75] Inventor: Anthony S. Ridolfo, Zionsville, Ind.

[73] Assignee: Eli Lilly and Company, Indianapolis, Ind.

[21] Appl. No.: 269,145

[22] Filed: Jun. 1, 1981

[51] Int. Cl.³ .......................................... A61K 31/625
[52] U.S. Cl. .................................................... 424/232
[58] Field of Search ......................................... 424/232

[56] References Cited

U.S. PATENT DOCUMENTS

Re. 29,608 4/1978 Evans et al. .................... 260/307 D

Primary Examiner—Stanley J. Friedman
Attorney, Agent, or Firm—James L. Rowe; Arthur R. Whale

[57] ABSTRACT

A therapeutic method for treating rheumatoid arthritis in which benoxaprofen plus aspirin are administered once a day and aspirin alone three times a day, all dosages being given at six hour intervals.

2 Claims, No Drawings

COMBINATION THERAPY FOR RHEUMATOID ARTHRITIS

This invention provides a novel treatment method for rheumatoid arthritis and other related inflammatory conditions, utilizing combination drug therapy in part, such as a combination of benoxaprofen, a lipoxygenase inhibitor, and a cyclo-oxygenase inhibitor such as aspirin. According to my invention, patients suffering from rheumatoid arthritis are administered from 200 to 800 milligrams of benoxaprofen and from 325 to 1170 of aspirin once a day and then at 6 hour intervals during the remainder of the 24 hour period from 325 to 1170 milligrams of aspirin alone. Preferably, the rheumatoid arthritis patient is given 600 mg. of benoxaprofen plus 975 milligrams (15 grains) of aspirin once a day and 975 milligrams of aspirin alone at 6 hour intervals. The regimen is then repeated on a daily basis.

The basis for the enhanced therapeutic effect from my novel process is the use of drugs acting at different sites of the inflammatory process. Improvement occurs even though blood levels of benoxaprofen are decreased with the concomitant addition of aspirin. It is an advantage of this invention that in the combination of a lipoxygenase inhibitor such as benoxaprofen and a cyclo-oxygenase inhibitor, each drug can be employed at dose levels lower than the commonly accepted effective dose for the individual drug.

Benoxaprofen, 2-(2-p-chlorophenyl-5-benzoxazolyl)-propionic acid, is disclosed in Example 2 of U.S. Pat. Re No. 29,608 reissued April 11, 1978.

The unexpected therapeutic utility of the process outlined above is illustrated by the following comparative studies. Nine patients with active rheumatoid arthritis were randomly assigned to one of three treatment groups on a double-blind basis. Each patient was given three identical capsules plus one tablet 4 times a day (every 6 hours). The capsules contained either aspirin or placebo and the tablet contained either benoxaprofen or placebo. The patients were examined every two weeks throughout the study. The following protocal was used. Patients were given a two week supply of medication packaged in four envelopes for each day's dose. At the end of a two week period, the envelopes were exchanged for a second two week supply, etc. All groups started out on placebos for two weeks. Next, each patient was given four weeks of active medication followed by two weeks of placebo, then four weeks of an alternate drug or drug combination, two weeks of placebo and finally four weeks of a second alternate drug or drug combination. If the rheumatoid arthritis flared up during the any given two week period, patients were instructed to return to the clinic at which time they were assessed and started on the next drug. It was necessary to restart four patients during the placebo periods.

Observations for each variable were averaged for each treatment period. This averaging resulted in four values per patient, one for each of the four treatment periods-placebo, benoxaprofen plus aspirin, benoxaprofen alone, and aspirin alone. The data were analyzed by the use of a 2-factor analysis of variance and Duncan's multiplle range test for each variable. In addition, a "pooled index" using three groups of variables was calculated according to the method of Smyth et al, *J. Rheumatol.* 4, 144-52 (1977). The advantage of the pooled index is that it can incorporate any number of variables measured to give a single overall measure of efficacy. Three pooled indecies were constructed. Pooled index I was based upon seven variables; joint pain—severity, morning stiffness—severity, grip strength, joint count, number of swollen joints, erythrocyte sedimentation rate (Westergren) and physician's evaluation. Pooled index II was based upon the same seven variables plus the following four additional variables: comfort index, patient's evaluation, range of motion, and convery fitness. Pooled index III was based upon the previous eleven variables plus the following four variables: walking time, circumference PIP's, circumference wrists, fatigue-severity. Table I which followes gives the results of these determinations.

TABLE I

| POOLED INDEX: TREATMENT MEANS | | | | |
|---|---|---|---|---|
| | Placebo | Aspirin | Benoxaprofen | Aspirin + Benoxaprofen |
| Pooled Index I (7 variables) | −1.63 | 0.16 | 0.52 | 0.95 |
| Pooled Index II (11 variables) | −1.64 | 0.23 | 0.51 | 0.92 |
| Pooled Index III (15 variables) | −1.34 | 0.22 | 0.41 | 0.72 |

According to Table I, benoxaprofen plus aspirin was significantly different from and better than placebo or aspirin alone. The combination was not significantly different (at the p=0.05 level) from benoxaprofen alone but the pooled indecies favored benoxaprofen plus aspirin in each instance.

Side effects encountered were those of aspirin and were more common with aspirin and aspirin plus benoxaprofen than with benoxaprofen alone.

While, in the above trial in humans, aspirin and benoxaprofen are administered separately, the two drugs can be combined in a suitable pharmaceutical formulation for oral adminstration. For example, aspirin and benoxaprofen can be mixed with one or more suitable pharmaceutically acceptable excipients and the mixture loaded into empty telescoping gelatin capsules such that each capsule contains 200 mg. of benoxaprofen plus 325 mg. (5 grains) of aspirin. A similar mixture, using some different excipients could be compressed into tablets such that each tablet contained 200-400 mg. of benoxaprofen and 5-10 grains of aspirin.

The above invention has been illustrated with respect to a single cyclo-oxygenase inhibitor, aspirin, but it will be apparent to those skilled in the art that other cyclo-oxygenase inhibitors such as fenoprofen, ibuprofen, napfroxen fluribiprofen, ketoprofen and the like can be employed in place of aspirin with a lipoxygenase inhibitor like benoxaprofen in treating rheumatoid arthritis with increased effectiveness and decreased side effects.

I claim:

1. A treatment method for rheumtoid arthritis which comprises administering to a patient suffering from rheumatoid arthritis a combination of from 200 to 820 mg. of benoxaprofen and 325 to 1170 mg. of aspirin once a day, from 325 to 1170 mg. of aspirin alone three times a day, all dosages to be administered at approximately six hour intervals; and then repeating the above daily dosage schedule on succeeding days.

2. A process according to claim 1 in which a combination of 600 mg. of benoxaprofen and 975 mg. of aspirin are administered once a day and 975 mg. of aspirin only three times a day.

* * * * *